(12) United States Patent
Shih (10) Patent No.: US 10,602,938 B2
(45) Date of Patent: *Mar. 31, 2020

(54) SYSTEMS AND METHODS FOR NONCONTACT ABLATION

(71) Applicant: Hue-Teh Shih, Houston, TX (US)

(72) Inventor: Hue-Teh Shih, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/278,696

(22) Filed: Feb. 18, 2019

(65) Prior Publication Data

US 2019/0274561 A1  Sep. 12, 2019

Related U.S. Application Data

(63) Continuation of application No. 14/046,457, filed on Oct. 4, 2013, now Pat. No. 10,244,955, which is a
(Continued)

(51) Int. Cl.
*A61B 18/14* (2006.01)
*A61B 5/04* (2006.01)
(Continued)

(52) U.S. Cl.
CPC ............ *A61B 5/04* (2013.01); *A61B 17/2202* (2013.01); *A61B 17/320068* (2013.01);
(Continued)

(58) Field of Classification Search
CPC ........ A61B 18/1492; A61B 2018/0016; A61B 2018/00196; A61B 2018/00273; A61B 2018/00214; A61B 2018/00351; A61B 2018/00577; A61B 2018/00994; A61B 2018/1407; A61B 2018/1465; A61B 2018/1467; A61B 2018/147; A61B 5/04; A61B 5/0422; A61B 17/2202;
(Continued)

(56) References Cited

U.S. PATENT DOCUMENTS

6,529,756 B1 * 3/2003 Phan ................... A61B 18/1492
600/374
10,244,955 B2 * 4/2019 Shih ................... A61B 17/2202
(Continued)

*Primary Examiner* — Thomas A Giuliani
(74) *Attorney, Agent, or Firm* — Sprinkle IP Law Group (57) ABSTRACT

Systems and methods for noncontact ablation of tissues or materials in/on the body using a luminal catheter and a catheter inserted into the lumen. In one embodiment, the luminal catheter is an ablation catheter and the other catheter is a recording/measurement/positioning catheter. The luminal catheter incorporates a noncontact ablation element such as an ultrasonic transducer. The luminal catheter can be inserted through the skin and into the body (e.g., into the heart) and the recording/measurement/positioning catheter can be inserted into the lumen so that the ablation and recording/measurement/positioning catheters are simultaneously positioned to record/measure the electrical activity of the target tissue and ablate the target tissue without causing the trauma that results from the introduction of additional catheters. Either of the ablation and recording/measurement/positioning catheters can be steerable, and either may incorporate recording/measurement electrodes.

15 Claims, 4 Drawing Sheets

Related U.S. Application Data continuation of application No. 12/177,202, filed on Jul. 22, 2008, now Pat. No. 8,585,695.

(51) Int. Cl.
| | |
|---|---|
| *A61B 17/22* | (2006.01) |
| *A61B 17/32* | (2006.01) |
| *A61B 5/042* | (2006.01) |
| *A61B 5/00* | (2006.01) |
| *A61B 18/00* | (2006.01) |
| *A61N 7/02* | (2006.01) |

(52) U.S. Cl.
CPC .......... *A61B 5/0422* (2013.01); *A61B 5/6857* (2013.01); *A61B 18/1492* (2013.01); *A61B 2017/320069* (2017.08); *A61B 2018/00577* (2013.01); *A61N 7/02* (2013.01); *A61N 7/022* (2013.01)

(58) Field of Classification Search
CPC .......... A61B 17/320068; A61B 2017/320069; A61N 7/02; A61N 7/022
USPC .......... 606/27, 41, 42, 49; 607/98–101, 113, 607/115, 116
See application file for complete search history.

(56) References Cited

U.S. PATENT DOCUMENTS

| | | | |
|---|---|---|---|
| 2004/0082948 A1* | 4/2004 | Stewart | A61B 18/1492 606/41 |
| 2006/0106295 A1* | 5/2006 | Jais | A61B 5/0422 600/374 |
| 2007/0038056 A1* | 2/2007 | Pappone | A61B 5/042 600/374 |
| 2007/0265610 A1* | 11/2007 | Thapliyal | A61N 7/02 606/27 |

* cited by examiner

SYSTEMS AND METHODS FOR NONCONTACT ABLATION

CROSS-REFERENCE TO RELATED APPLICATIONS

This application is a continuation of U.S. patent application Ser. No. 14/046,457 entitled "Systems and Methods for Noncontact Ablation", by Hue-Teh Shih, filed on Oct. 4, 2013, and issued as U.S. Pat. No. 10,244,955 on Apr. 2, 2019, which is a continuation of U.S. patent application Ser. No. 12/177,202 entitled "Systems and Methods for Noncontact Ablation", by Hue-Teh Shih, filed on Jul. 22, 2008, and issued as U.S. Pat. No. 8,585,695 on Nov. 19, 2013, both of which are incorporated by reference as if set forth herein in their entirety.

BACKGROUND

Field of the Invention

The invention relates generally to medical devices and methods for their use. More particularly, the invention relates to systems and methods for ablating tissues or materials within the body.

Related Art

In the medical field, ablation is used as a therapy in the treatment of various diseases (e.g., skin spots, snoring, tumors, hemorrhage, arrhythmia, atherosclerosis) and has a number of modalities (e.g., DC, RF, microwave, laser, ultrasound, chemical, cryogenic, rotary blade).

An ablation can be performed to transect or otherwise alter the function of some tissue. For example, fatty deposits or plaque which present an obstruction in an artery can be removed using a laser to break up the obstruction, thereby restoring blood flow. In another example, cardiac muscle can be burned to create a lesion which obstructs the conduction of (aberrant) electrical signals within the heart (that is, the lesion interrupts abnormal electrical conduction in the heart, therefore cures abnormal heart rhythms.)

The treatment of cardiac arrhythmia is of particular interest, as it is debilitating or even deadly and is one of the most common disorders in clinical practice. In the United States, many patients die every year due to specific heart rhythm disorders that are caused by abnormal, rapid beats. For example, it is estimated that 3 million people in the United States have atrial fibrillation, one of the most common cause of stroke. Additionally, atrial fibrillation is also related to heart failure. A number of pharmacologic and surgical therapies are available to treat these disorders.

Percutaneous translumenal (catheter-based) ablation is a minimally invasive therapy and has been shown to be relatively safe and effective in treating selected heart rhythm disorders. In a typical cardiac ablation procedure, several catheters are advanced through the venous or arterial systems and positioned inside the heart. These are used to assess the etiology of the disease and then to treat it.

Various procedures are employed in catheter-based ablation therapy. Typically, a single percutaneous procedure to ablate cardiac tissue is iterative and makes use of multiple sheaths and catheters in multiple steps. First, catheters are maneuvered into various positions to denote the location and measure the timing of cardiac activation. This is followed by the placement of an ablation catheter in contact with the cardiac tissue at a location where electrical activity is to be disrupted. The ablation catheter is used to burn or freeze the engaged tissue, altering the tissue behavior. Additional measurements are then made to reassess the cardiac function. This process is performed iteratively, alternating measurement and ablation, until the cardiac activation and resulting heart rhythm are modified as desired.

Multiple factors affect the success of an ablation procedure. For example, because it is essential to have an accurate diagnosis of the type of arrhythmia and localization of the culprit(s) of the arrhythmia to achieve success in the ablation procedure, it is often necessary to place multiple electrode catheters in the heart. These catheters can interfere with one another as they are manipulated, and the use of multiple catheters can also increase the risks of clot formation and injury to the cardiac tissue.

Another factor is contact with the tissue to be ablated. Conventional devices such as those that use radio frequency energy, cryogenic material, and laser energy to ablate tissue are designed to ablate the target tissue when the catheter is in direct contact with the tissue. Tissue contact is critical, but various factors affect the contact and contact pressure between the tissue and ablation element, including the anatomy of the target and the adjacent structure, the design of the catheter itself, and the relationship between the catheter and the anatomy, to list only a few. Additionally, the presence of blood between the tissue and the ablation element severely decreases the efficacy of radio frequency, cryogenic, and laser ablation. The tissue characteristics can also affect the efficacy of the ablation energy. For instance, it is difficult for radio frequency and cryogenic materials to penetrate the superficial scar tissue and reach the deeper muscular tissue of interest.

Another factor affecting the success of an ablation procedure is the inability to reliably (re)position catheters. The positioning not only affects the ability to take consistent measurements with a recording electrode, but also affects the ability to reliably ablate the intended target tissue. For instance, mispositioning of the ablating element/electrode can result in failure to return to an ablation site to complete a burn (an ablation), or can result in gaps in a line of burns when creating a linear lesion. These factors can make it difficult to apply the therapy, render the therapy ineffective, or even enhance the disease (e.g., make the cardiac tissue proarrhythmic).

It would therefore be desirable to provide systems and methods for ablating tissue in the body which are less complicated and more reliable and effective than prior ablation systems and methods.

SUMMARY OF THE INVENTION

One or more of the problems outlined above may be solved by the various embodiments of the invention. Broadly speaking, the invention includes systems and methods for ablating tissues or materials in/on the body.

One embodiment comprises a system for noncontact ablation of tissues or materials in or on the body using a sheath-like luminal catheter and a second catheter that is inserted into the lumen of the first catheter. In one embodiment, the lumen catheter is a recording/ablation catheter that also serves as the sheath for the other catheter, and the other catheter is a recording/positioning catheter. The luminal catheter incorporates a noncontact ablation element such as an ultrasonic transducer, in addition to recording electrodes. The luminal catheter can be inserted through the skin and into the body (e.g., into the heart, tubular structures such as veins, or other organs or tissues) via conventional methods. The recording/positioning catheter can be inserted into the lumen so that the recording/ablation catheter and the recording/positioning catheter are simultaneously positioned to record the electrograms and ablate the target tissue without causing the potential clots and trauma that can result from the superfluous catheters used in conventional ablation procedures.

Either or both of the ablation and recording/positioning catheters can be steerable, and either or both may incorporate recording electrodes. The recording/positioning catheter may be configured with a loop or other shape to aid in maintaining proper positioning in the body. The loop may be off-axis with respect to the main body of the system in order to allow adjustment of the distance between the ablation element and the target tissue. The noncontact ablation element(s) in the ablation catheter may, for example, radiate energy in a circumferential or semi-circumferential pattern. The ablation catheter is particularly well-suited for applications in which the target is shaped in a tubular or funnel-like fashion, but is not limited to such structures.

An alternative embodiment comprises a method for noncontact ablation of target tissue that includes providing a first catheter which has a lumen and a second catheter configured to fit within the lumen of the first catheter. One of the first and second catheters is a noncontact ablation catheter and one is a recording/positioning catheter. The method further includes positioning the first catheter in a body and placing the second catheter within the lumen of the first catheter. One or more recordings are made using the recording/positioning catheter, and target tissue in the body is ablated using the ablation catheter. The recordings are typically, but not limited to, electrograms.

Numerous additional embodiments are also possible.

BRIEF DESCRIPTION OF THE DRAWINGS

Other objects and advantages of the invention may become apparent upon reading the following detailed description and upon reference to the accompanying drawings.

While the invention is subject to various modifications and alternative forms, specific embodiments thereof are shown by way of example in the drawings and the accompanying detailed description. It should be understood that the drawings and detailed description are not intended to limit the invention to the particular embodiments which are described. This disclosure is instead intended to cover all modifications, equivalents and alternatives falling within the scope of the present invention as defined by the appended claims.

DETAILED DESCRIPTION OF EXEMPLARY EMBODIMENTS

One or more of the problems outlined above may be solved by the various embodiments of the invention. It should be noted that the embodiments described below are exemplary and are intended to be illustrative of the invention rather than limiting.

Broadly speaking, the invention includes systems and methods for ablation of tissue in the body. In the medical field, many ablation devices and procedures have been developed to treat a variety of conditions. In particular, catheter-based devices have been developed to deliver therapies within various structures and spaces within the body. For example, the devices can be used for recanalizing atherosclerotic vessels, elimination of endometriosis on a uterine wall, disruption of conduction paths associated with reentrant tachycardia, and even the occlusion of blood vessels.

One embodiment consists of a combination of recording and ablation catheters. The ablation catheter is a sheath-like catheter that has an ultrasonic transducer affixed to the distal end and may also be configured to record data from electrodes on the catheter. The recording/ablation catheter is configured to accept a positioning catheter through its lumen. The positioning catheter may serve to guide and anchor the ablation/recording catheter so that it can be accurately positioned. The positioning catheter may also include electrodes for recording tissue data. The recording/ablation catheter is free to move along the recording/positioning catheter and stands off from the tissue to be ablated (being supported by the recording/positioning catheter). When deployed, the recording/positioning catheter extends beyond the distal tip of the recording/ablation catheter and engages some structure beyond the ablation catheter. The ultrasonic transducer is configured to emit energy in a ring perpendicular to the recording/ablation catheter body. The recording/positioning catheter is configured to record signals used to determine the mechanism of arrhythmia, the target of ablation, and the efficacy of an ablation. Recordings made during the ablation may be used as feedback to control the ablation Before describing the invention in detail, it will be helpful to understand how certain terms are used in the present disclosure. Very simplified descriptions of both normal and abnormal conduction in the heart will also be presented to aid in the understanding of cardiac tissue ablation and related devices and procedures.

"Tissue," as used herein, refers to any material in the body, so tissue which is the target of ablation should not be narrowly construed to include only biological tissue, but may include targeted material, whatever its makeup or origin (e.g., muscle, tumor, plaque).

"Catheter" refers to a rod- or tube-like device inserted into the body. Many catheters, such as those used in cardiac ablations, are very narrow (similar to a wire) so that they can be inserted through the skin and into a blood vessel. This allows the catheters to provide access to, or to deliver some distal end-effector (therapy), to some site in the body. Catheters may have many different configurations (e.g., lumen, non-lumen, etc.) and many different functions (e.g., positioning, recording, ablation, etc.)

"Distal" refers to a point or end of an object which is opposite a reference point on the object. In regard to a catheter, the reference point is typically the end of the catheter external to the body, so the distal end of the catheter is the end which is inserted into the body.

"Proximal" refers to a point or end of an object which is nearest the reference point on the object. In reference to a catheter, the proximal end of the catheter is the end which is external to the body and is typically in the hands of the clinician.

A "lumen" is a passage or duct. A lumen in a catheter or sheath is a duct through the catheter. For the purposes of this disclosure, a "lumen catheter" or "luminal catheter" is a sheath-like catheter or hybrid catheter-sheath which has a lumen inside the catheter through which another catheter can be inserted into the body.

"Contact" refers to the physical contact between items such as a catheter and targeted tissue. For proper operation, a contact ablation device must directly engage the targeted tissue.

"Non-contact" refers to the lack of physical contact between items. For example, a "non-contact" ablation device is designed to stand off from the targeted tissue and ablate the tissue without directly contacting the tissue.

Conduction in the heart will now be briefly described.

The heart is constructed of muscles (myocardium), valves, and a control system. The myocardium not only provides the force behind the pumping action but supports the conduction of electrical signals. The heart also has a specialized conduction system whose purpose is to initiate and coordinate the pumping action of the muscle cells. One part of this system is the sinoatrial (SA) node. The SA node is the pacemaker of the heart and is responsible for initiating the heart beat. The atria first receive the signal from the SA node, pumping blood into the ventricles. Simultaneously, the signal travels to the atrioventricular (AV) node. The signal then travels into the lower ventricles by means of Purkinje fibers causing the ventricles to contract "upwards" towards the valves.

For a given myocardial cell, there is a cycle of activation, recovery and waiting. Typically, a cell has an external stimulus such as from a neighboring cell (though a cell can spontaneously depolarize, which is referred to as "automaticity"). When activated, the cell "depolarizes" causing it to contract, and then "repolarizes". The cell's activity stimulates neighboring cells (as will those cells) resulting in a "wave" of activity through the myocardium (a.k.a., activation front). There is a "refractory" period during this cycle when the cell cannot be stimulated. If a cell is ablated, it becomes nonfunctional and can no longer be stimulated, nor can it conduct a wave/signal to its neighbors.

There are a number of conditions that result in the disruption of the normal cardiac rhythm. One of these is sick sinus syndrome, which is the result of erratic SA node activity. Alternatively, the SA node activity can be inappropriately fast, causing inappropriate sinus tachycardia. In a case of inappropriate sinus tachycardia, the SA node can be ablated (burned or frozen), destroying the nodal tissue and thereby slowing down the rate of its firing to control the tachycardia.

Another disruption of normal cardiac rhythm is caused by the aberrant behavior of a cardiac cell or small number of cardiac cells that take over the pacing of the heart from the SA node. These cells prematurely depolarize, thereby initiating the depolarization of neighboring cells and resulting in an unwanted wave of electrical activity. This unwanted origin of electrical activity (a.k.a., ectopic focus) can be eliminated by destroying the offending cells with a localized burn (or freeze), allowing the SA node to again properly pace the heart.

Yet another arrhythmia is caused by the conduction of signals from an atrium directly to a ventricle (outside the specialized conduction system) via an (unwanted) accessory pathway. This pathway can be obstructed by burning (or freezing) the associated tissue.

Another form of arrhythmia is reentrant tachycardia, which is the result of a circuit incorporating tissue that effectively causes a signal delay. The delayed signal then initiates activity in adjacent tissue. The delayed signal re-enters the tissue, resulting in a self-perpetuating electrical circuit.

These are but a few simple examples. In each case, an ablation can be used to "correct" the abnormality. However, to do so requires the careful use of an ablation system to properly place an appropriately sized lesion.

As noted above, the treatment of cardiac arrhythmia is of particular interest since arrhythmia is one of the most common disorders in clinical practice and leads to so many fatalities. While a number of pharmacologic and surgical therapies are available to treat these heart rhythm disorders, catheter ablation often proves to be curative.

Percutaneous transluminal catheter ablation is a minimally invasive therapy in which a series of catheters are inserted through the skin and advanced through the venous or arterial systems and positioned inside the heart or other tissues to either assess the etiology of or to treat the disease. Typically, a catheter or series of catheters are used to record the electrical signals from the location of interest and measure timing of cardiac activation followed by placement of an ablation catheter. The ablation catheter is then used to burn (or freeze) the engaged tissue, altering the tissue behavior. This process is performed iteratively, thereby modifying the heart rhythm. Percutaneous transluminal catheter ablation has been shown to be relatively safe and effective, for example, in treating selected heart rhythm disorders.

Ablation procedures typically employ a combination of devices appropriate to the task. Many of the devices are not directly involved in the ablation of the target tissue. These include, for instance, recording/measurement catheters that aid in determining performance of an organ/structure, determining the etiology of a disease, or in evaluating the efficacy of an ablation. Positioning/anchoring catheters/sheaths may also be used to guide placement of the ablation and recording/measurement catheters to the desired locations in the heart or other tissues.

In the past, direct current (DC) ablation was used for the treatment of heart rhythm disorders, but radiofrequency (RF) ablation has supplanted it as the therapy of choice. For example, RF catheter ablation has revolutionized the treatment of supraventricular tachycardias (i.e., inappropriate sinus tachycardia, Wolff-Parkinson-White syndrome, atrioventricular nodal reentrant tachycardia, atrial tachycardia, and atrial flutter.)

Generally, a cardiac ablation entails directing a sufficient amount of energy into the tissue through a catheter in such a way as to produce a lesion within the heart tissue. Typically, radiofrequency (RF) energy is used. The energy is directed into the myocardium (cardiac muscle) at a spot on the endocardium for a period great enough to produce a lesion sufficiently large to either destroy an ectopic focus or to obstruct an unwanted pathway. The RF ablation requires that the active electrode of the catheter be placed in continuous, direct contact with the target tissue for the prescribed period. Afterwards, recordings and measurements are made to determine if the lesion has the desired effect. If not, the ablation catheter may need to be (re)placed at the same ablation site to enlarge the lesion or placed at another (usually adjoining) site to create an additional (larger) lesion. This process continues until the procedure is successful or until the procedure is terminated for other reasons.

Figure 1:
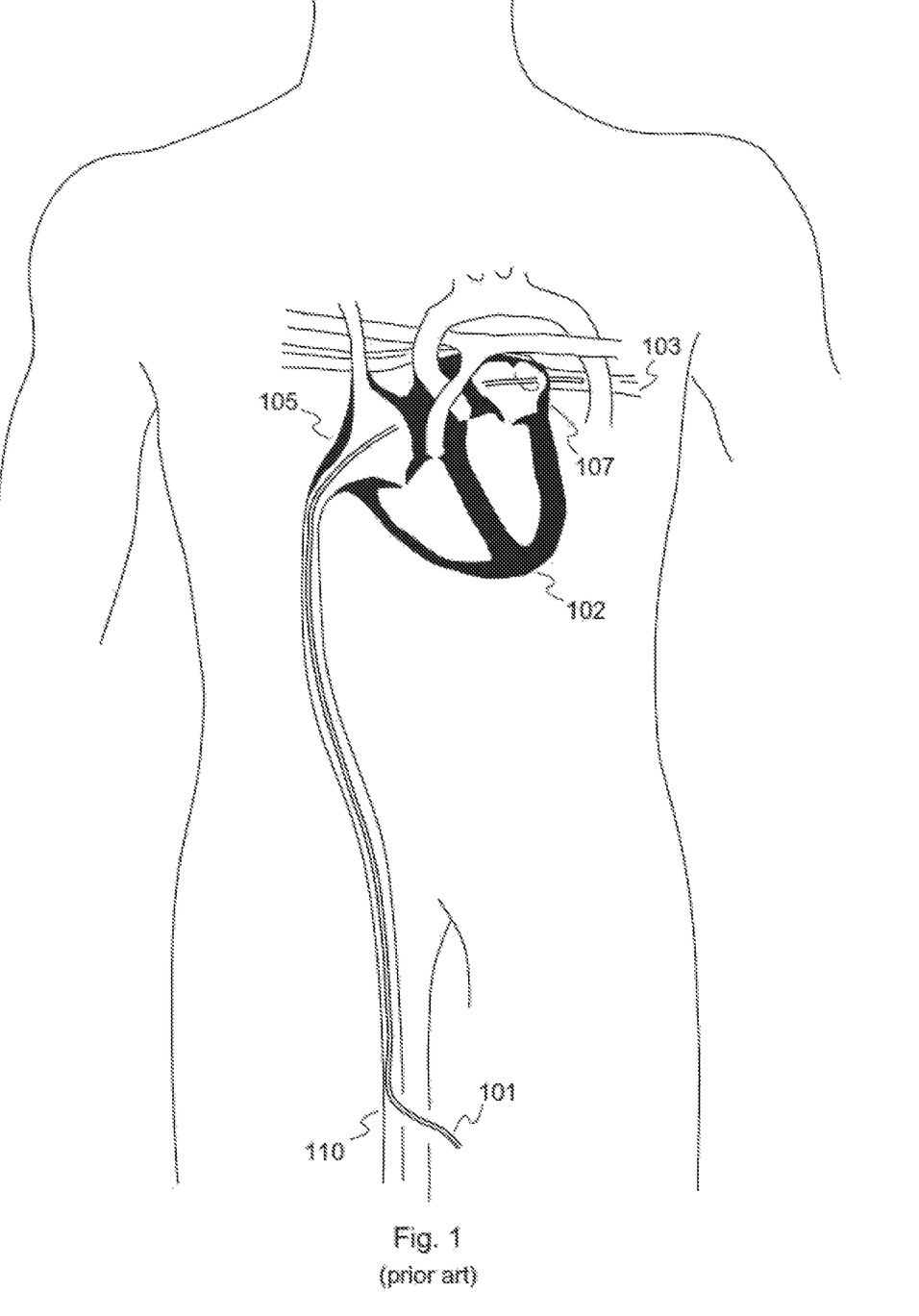
FIG. 1 is a diagram illustrating catheter placement within a body for a cardiac ablation procedure in accordance with the prior art.

FIG. 1 illustrates a conventional configuration for ablation within a heart. Access to the heart (102) is provided through the circulatory system itself, typically a femoral vein (110). Other vessels (e.g., 120) can also be used. A catheter or series of catheters (e.g., 101) are advanced into the heart and are configured to make recordings in and even pace the heart. The catheters may, for example, be advanced into the right atrium (105), though the interarrial septum to the left atrium (107) and into pulmonary vein 103.

Typically, multiple catheters are placed simultaneously. On occasions, due to limited access and inability to simultaneously record/measure from the ablation catheter, the same access site has to be shared by the recording/measurement catheter and the ablation catheter. In this case, a recording/measurement catheter is inserted, recordings/measurements are made, and then the recording/measurement catheter is withdrawn. An ablation catheter (101) is then advanced into the heart and positioned at a predetermined site. The process is performed iteratively as necessary. A number of burns are then performed. It is not uncommon for ablation catheters to have to be removed and cleaned before being reintroduced to complete subsequent burn(s). Often, blood clots form on the electrodes of an RF catheter, making it ineffective. Also, catheters of differing configurations may have to be used.

Only one catheter is depicted in FIG. 1, but multiple catheters may be used simultaneously. For instance, a conventional pulmonary vein isolation procedure that uses multiple catheters simultaneously requires four components: a first positioning/anchoring sheath; a recording/measurement/positioning catheter which is inserted through the first sheath; a second sheath; and an ablation catheter which is inserted through the second positioning/anchoring sheath. While the simultaneous use of these catheters avoids the need to repeatedly withdraw and insert the catheters, the use of multiple catheters is much more invasive than the use of a single catheter at a time (or a single luminal catheter with a single ablation catheter inserted through the luminal catheter that functions both as a sheath and a recording/measurement/positioning/anchoring catheter).

In conventional cardiac ablation procedures, gaps can make the ablation ineffective and can possibly be arrhythmogenic (possibly creating a circuit around the lesion). A labyrinth-like arrangement of conductive tissue resulting from an ablation can effectively create a circuit with a delay which is sufficient to reinitiate a wave of activation after the refractory period of the local cells, but before it would be initiated by proper pacing.

Figure 2A:
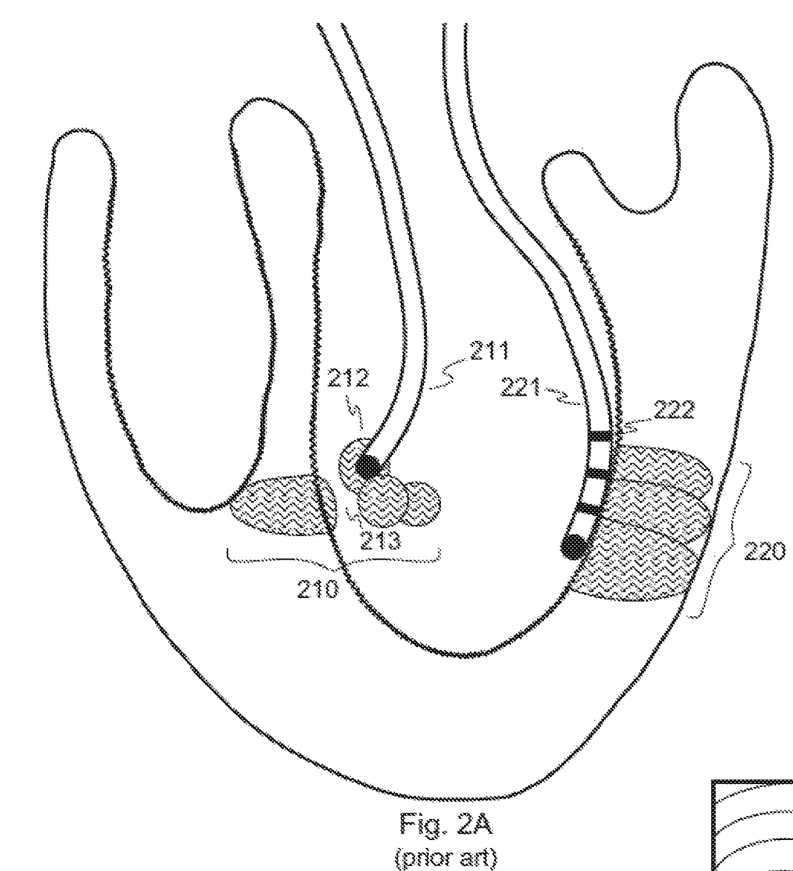
FIGS. 2A and 2B are diagrams illustrating the creation of lesions in cardiac tissue using conventional ablation techniques.
Figure 2B:
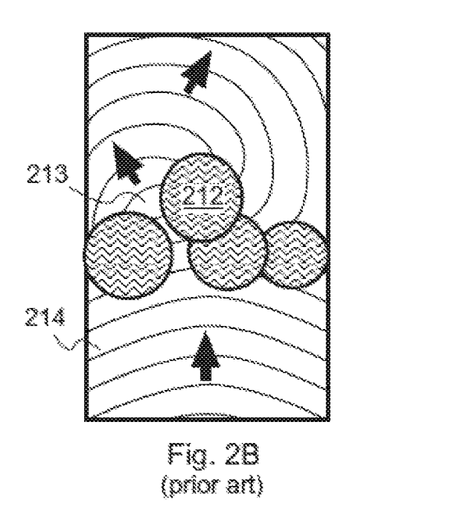

FIGS. 2A and 2B are diagrams illustrating the creation of lesions in cardiac tissue using conventional ablation techniques. FIG. 2A shows a cutaway view of a heart. On the left side of the figure, a single-element contact ablation catheter (211) is shown. On the right side of the figure, a multiple-element contact ablation catheter (221) is shown. (It should be noted that the two different types of ablation catheters may not be used at the same time.)

Single-element ablation catheter 211 must be repositioned in a series of adjacent sites so that a series of lesions can be made. The purpose of creating the series of lesions is to overlap the lesions so that a longer, linear lesion is produced. The linear lesion is intended to transect an undesired electrical pathway and thereby disrupt abnormal activation of the cardiac cells. As shown in the figure, incorrect positioning of catheter 211 can result in corresponding mis-positioning of the lesions. For example, lesion 212 is not aligned with the remainder of the lesions 210 created by catheter 211, so there is a gap 213 between the lesions.

FIG. 2B illustrates the propagation of an activation front up to and through lesions 210. The activation front is indicated by the lines (e.g., 214) in the figure. In the case of lesions 210, a remapping of the activation after the ablation would likely show the need for an additional burn to close gap 213. Thus, the misplacement of the catheter results in unnecessary damage to the tissue and adds time to the procedure. Another difficulty may arise because of temporary swelling around the lesions—it is possible that the gap would not be immediately evident. This may add more time to the procedure (in the best case) or possibly require an additional procedure to correct the problem if it is not found during the initial procedure.

Referring again to FIG. 2A, procedures using multiple-element contact ablation catheter 221 may also experience problems in creating the desired lesions. For instance, because the ablation elements on the catheter are positioned along the length of the catheter, it may be difficult to position the catheter to create a lesion that is transverse to the direction from which the catheter is inserted (i.e., into the page in the figure). Also, it may be difficult to ensure that the entire length of the catheter along which the ablation elements are positioned is in contact with the tissue. As depicted in FIG. 2A, ablation element 222 of catheter 221 is not in contact with the tissue, so the element cannot reliably deliver the intended dosage of energy to ablate the tissue. As a result, lesions 220 may not serve the intended purpose.

Figure 3A:
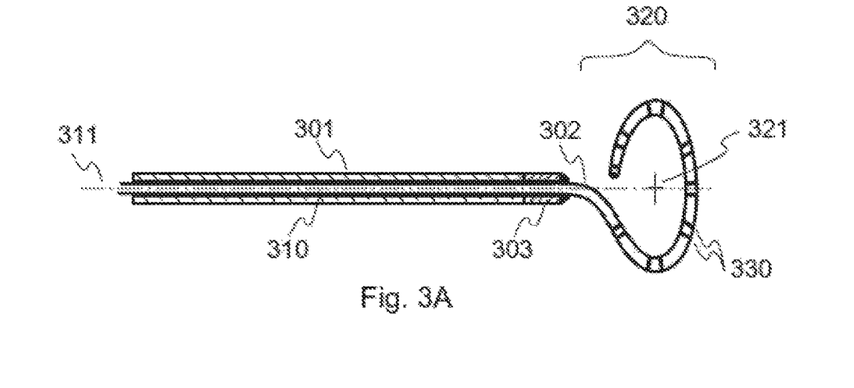
FIGS. 3A-3C are diagrams illustrating several embodiments of the invention.
Figure 3B:
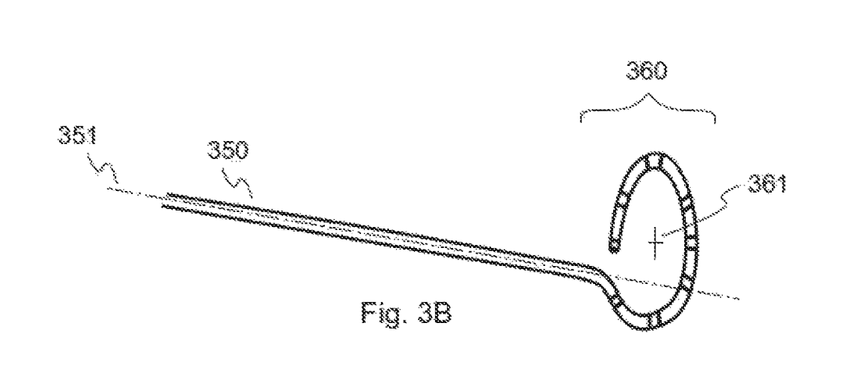
Figure 3C:
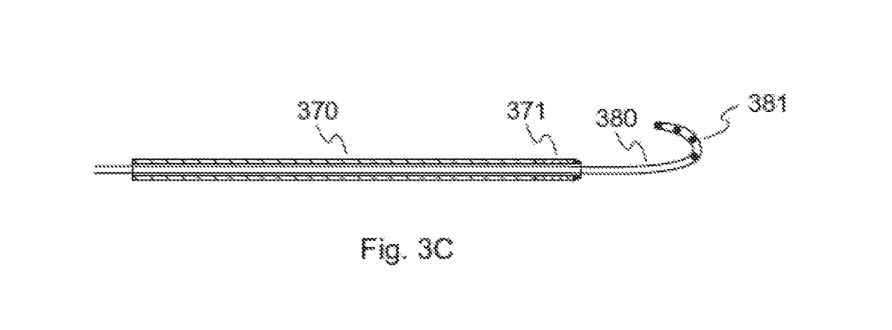

FIGS. 3A-3C are diagrams illustrating several embodiments of the invention. FIG. 3A is an illustration of an exemplary system in accordance with one embodiment. This embodiment comprises an ablation luminal catheter 301 and a recording/positioning catheter 302. Both ablation catheter 301 and recording/positioning catheter 302 may also serve other purposes, such as recording catheters, anchoring catheters, etc. Ablation catheter 301 includes a non-contact ablation element 303 which is located at or close to the tip of the catheter. Non-contact ablation element 303 may, for example, be an ultrasound transducer which is configured to deliver energy in the form of ultrasonic waves to the tissue targeted for ablation. The ultrasound energy destroys the tissue by heating the tissue, creating lesions that can block unwanted electrical pathways. The ultrasound energy, however, can be delivered from a stand-off position. That is, the ablation element need not be in contact with the target tissue. The ultrasonic waves can travel through fluids between the ablation element and the tissue so that the target tissue, rather than the intervening fluid, is destroyed. As noted above, recording elements can be mounted at other locations on the luminal catheter in order to provide recordings and measurements that complement those of the recording/positioning catheter.

Ablation catheter 301 is itself a luminal catheter. Recording/positioning catheter 302 can therefore be inserted within the lumen of ablation catheter 301, much like using a sheath. Conventionally, a sheath in an ablation procedure serves no purpose other than to provide a conduit through which a functional (e.g., ablation or recording/measurement) catheter is inserted. By incorporating an ablation element and possibly several recording elements onto the luminal catheter/sheath (or alternatively incorporating a lumen into an ablation/recording catheter), twice as many functional instruments can be inserted into the body with no increase in the invasiveness of the procedure and no increase in the trauma to the affected tissue caused by the insertion procedures. This provides a substantial advantage over conventional techniques. With regard to procedures in which separate ablation and recording/measurement catheters are repeatedly inserted and withdrawn from the body, this embodiment reduces the amount of time required to perform the procedure and reduces the possibility of catheter positioning errors. With respect to procedures in which multiple catheters are simultaneously inserted into the body, this embodiment reduces the amount of space occupied by the surgical instruments because it reduces the number of catheters and sheaths, from typically four (two sheaths, an ablation catheter and a recording/measurement catheter) to two (a luminal catheter/sheath for ablation and recording that also serves as the conduit for a second recording/positioning/anchoring catheter), thereby reducing the trauma.

Recording/positioning catheter 302 has a main body 310 and a distal portion 320 which includes an array of electrodes (e.g., 330). The distal portion 320 can be formed into a loop. The loop is placed in contact with the tissue (e.g., the myocardium or blood vessel wall) and enables the accurate positioning and stable anchoring of ablation catheter 301 (or more specifically ablation element 303), which can be moved forward or backward over main body 310. In the embodiment of FIG. 3A, loop portion 320 is substantially concentric with and perpendicular to the axis of main body 310 of catheter 302. As a result, if loop center 321 is coaxial with a cavity in which the catheter is inserted, ablation element 303 remains substantially centered in the cavity, regardless of the movement of ablation catheter 301 over main body 310.

In an alternative embodiment (depicted in FIG. 3B), the main body 350 of the recording/positioning catheter is off-axis rather than being concentric with loop portion 360. That is, the axis 351 of main body 350 does not pass through the center (361) of loop portion 360. This embodiment is useful because, when loop portion 360 is positioned against the walls of a cavity, movement of the ablation catheter over main body 350 changes the position of the ablation element with respect to the axis of the cavity. In other words, when the ablation catheter is moved forward (toward the loop), the ablation element moves closer to the wall of the cavity, and when the ablation catheter is moved backward (away from the loop), the ablation element moves farther from the wall of the cavity. By changing the distance between the ablation element and the wall of the cavity (which contains the target tissue), the dosage of energy delivered to the tissue and the area of the target tissue can be adjusted.

Another alternative embodiment is shown in FIG. 3C. FIG. 3C shows an ablation system including an ablation catheter 370 (with ablation element 371) and a recording/positioning/anchoring catheter 380 which is inserted through the lumen of the ablation catheter. In this embodiment, recording/positioning/anchoring catheter 380 does not have a loop at the distal end of the catheter, but instead has a hook-shaped portion. This hook-shaped portion serves essentially the same purpose as the loop portion of the other embodiments in that it is placed against some part of the tissue to stabilize the recording/positioning catheter and allow the ablation catheter to be positioned and anchored by sliding it over the recording/positioning/anchoring catheter.

The loop shape can be an integral (fixed) feature of the catheter or (re)configurable. The catheter may have a lumen and the distal portion of the catheter may be constructed of a flexible material that takes the shape of a wire that is introduced into the lumen. Alternatively, the shape may be manipulated, as in a deflectable/steerable catheter. In some embodiments, the luminal catheter/sheath may be deflectable/steerable as well.

Another purpose of the loop portions and hook portions of the recording/positioning/anchoring catheters is to enable recording and measurements of the tissue characteristics (e.g., electrical potentials). The recording/positioning/anchoring catheters therefore include electrodes (e.g., 330, 381) positioned on the loop and hook-shaped portions. The electrodes are coupled to recording/measurement/stimulation unit(s) at the proximal end of the catheter. The recording/measurement/stimulation units are configured to transmit stimulus signals to the electrodes if necessary and to receive signals from the electrodes via wiring through the catheter. When the recording/positioning/anchoring catheters are positioned with the respective loop/hook portions against the tissue, the electrodes can be used to record and measure the tissue characteristics. The electrodes may be in contact with the tissue, or they may not be in contact with the tissue, depending upon the circumstances. Because the recording/positioning/anchoring catheters and corresponding electrodes can remain in place during the ablation procedure, consistent before-and-after recordings and measurements can be made. The electrodes are used in the assessment/evaluation of the effectiveness of an ablation. The electrodes can be positioned to record electrical (cardiac) signals or to stimulate (pace) the heart.

It should be noted that additional electrodes can be positioned on the ablation luminal catheter/sheath. These electrodes may, for example, be placed on the body of the ablation catheter on the side of the ablation element opposite the distal end of the catheter. The electrodes of the ablation catheter and recording/positioning/anchoring catheter/sheath would therefore be on opposite sides of the lesion created by the ablation procedure. This allows the operator to assess the effect of the ablation, i.e. whether there is a disconnection or disruption of electrical conduction between the distal and the proximal portion of the tissue, without the need to replace the ablation ensemble with the recording ensemble for this purpose, thus shortening procedure time.

Figure 4:
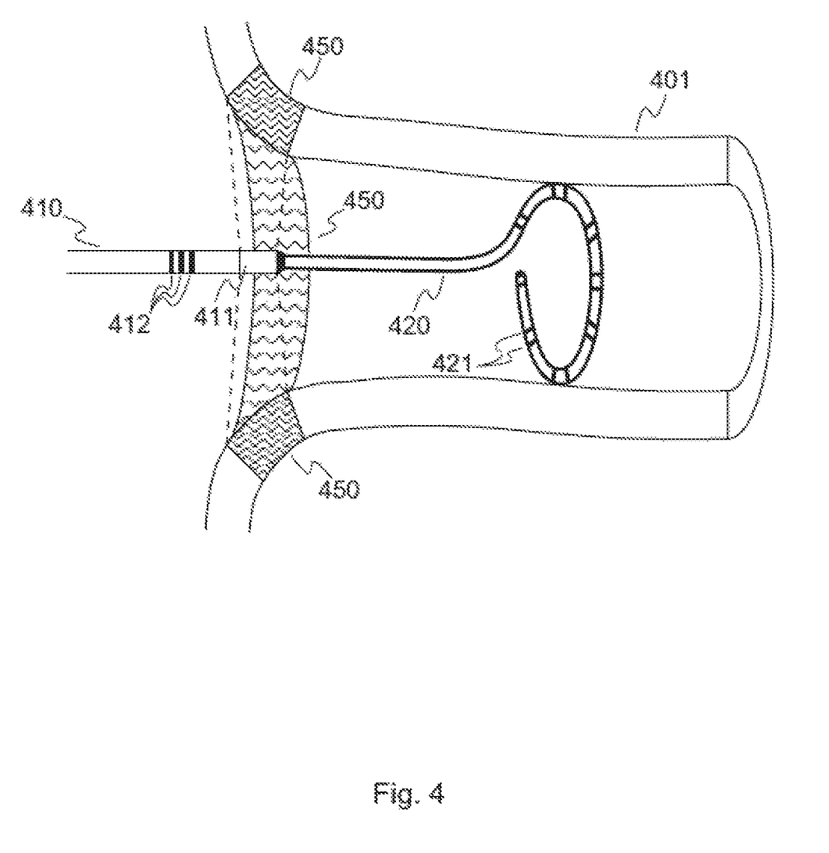
FIG. 4 is an ablation system in situ in accordance with one embodiment.

FIG. 4 illustrates one embodiment of the present system positioned for an ablation procedure in a pulmonary vein 401. Ultrasound transducer 411 is mounted at the distal end of a sheath-like ablation catheter 410. The ablation catheter has a lumen and is configured with recording/positioning catheter 420 in the lumen. Positioning catheter 420 is configured in this embodiment to serve recording/measurement functions as well as positioning and anchoring the ablation catheter. Mounted on positioning catheter 420 is an array of electrodes (421) which are positioned in contact with the walls of the pulmonary vein near the entrance to the left atrium. Mounted on the body of the ablation catheter are reference electrodes 412. Recordings and measurements from some combination of electrodes (and references) are made before, during, and after an application of energy (e.g., ultrasound energy) for ablation. The recordings and measurements are used to make assessments of the disease state and of the treatment effect.

Ultrasound transducer 411 is configured in this embodiment to emit energy in a circumferential pattern and to thereby produce a linear or even circumferential burn which results in a continuous lesion such as 450. Lesion 450 isolates the tissue of the pulmonary vein from the cardiac tissue In an alternative embodiment, the transducer could be configured to generate a partial circumferential burn, or a narrower or shorter burn. The shape and extent of the burn and the characteristics of the resulting lesion will depend upon various factors, such as the characteristics and positioning of the ablation catheter.

A procedure using the present system could take different forms. The ablation catheter/sheath could be introduced first and the recording catheter then advanced through the ablation catheter/sheath. The recording catheter could be introduced first and the ablation catheter/sheath then advanced over the recording catheter. A guide wire could be positioned first with either or both of the ablation and recording catheters then advanced.

In one embodiment, the recording/positioning catheter is introduced and positioned within the heart. Some number of recordings/measurements is made and an ablation site (or sites) is determined. An ablation catheter/sheath such as one described in connection with FIG. 3 or 4 is advanced over the recording/positioning catheter to the required position in the heart. Baseline measurements are made with the ablation catheter in place. Then, ablation is performed while making additional recordings/measurements. When it appears that a sufficiently large lesion has been created, the ablation is stopped. With the ablation system still in place, recordings/measurements continue and the burn is assessed. If needed, additional burns are made and the ablation procedure is concluded. Note that the ablation catheter/sheath need not be removed to allow for measurements to be made. The result is a more efficient procedure than with conventional systems. Also, with an ablation element such as the ultrasonic transducer, the formation of blood clots or charring on the device is not as likely as with conventional ablation systems such as those that use radio frequency energy, so fewer or no cleanings are necessary.

There may be numerous alternative embodiments of the system. It is contemplated that the invention is not limited to ultrasound ablation, and various different non-contact ablation modalities can be used. The selection of materials from which a catheter body and other components can be constructed is also quite varied and may include such materials as polyurethane, silicone, PTFE, steel, copper and carbon. The systems described above comprise an ablation catheter/sheath with a lumen within which the recording/positioning catheter is positioned. The system can alternatively comprise a recording/measurement catheter with a lumen, within which the ablation catheter is positioned. The distal portions of the catheters can be of a variety of shapes (e.g., circular, semi-circular, hook, Y, basket). The catheters may comprise lumens to make use of guide wires for positioning or shaping purposes. A deflection mechanism could be incorporated for purposes such as steering or shaping the catheters. There are many possible arrangements of electrodes for testing, recording, measurement, pacing, reference, etc.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein and recited within the following claims.

What is claimed is:

1. A method comprising:
providing a first catheter which has a lumen and a second catheter which fits within the lumen of the first catheter, wherein one of the first and second catheters is a noncontact ablation catheter, and wherein one of the first and second catheters is a positioning catheter;
placing the first catheter in a body and placing the second catheter within the lumen of the first catheter;
positioning the positioning catheter against non-target tissue in the body;
making one or more electrical recordings and measurements using one or more electrodes on the positioning catheter and one or more electrodes on the ablation catheter;
moving the ablation catheter in a telescoping fashion with respect to the positioning catheter while the positioning catheter is in contact with the non-target tissue in the body and thereby adjusting an ablation position of the ablation catheter with respect to the body and a location of target tissue in the body to be ablated; and
radiating energy from one or more ablation elements on the ablation catheter substantially perpendicularly to an axis of the noncontact ablation catheter only into a predefined circumferential or semi-circumferential pattern on the target tissue without reflection and without contact between the target tissue and the ablation catheter.

2. The method of claim 1, wherein making the one or more electrical recordings and measurements and radiating energy to the target tissue are performed simultaneously.

3. The method of claim 1, wherein a first portion of the one or more electrical recordings and measurements are made before energy is radiated to the target tissue and a second portion of the one or more electrical recordings and measurements are made after energy is radiated to the target tissue.

4. The method of claim 1, wherein the one or more electrodes on the positioning catheter are positioned on a first side of the target tissue and the one or more electrodes on the ablation catheter are positioned on an opposite side of the target tissue, and wherein the one or more electrical recordings and measurements are made between the one or more electrodes on the positioning catheter and the one or more electrodes on the ablation catheter.

5. The method of claim 1, wherein radiating energy to the target tissue comprises delivering ultrasonic energy to the target tissue from a position which is not in contact with the target tissue.

6. The method of claim 1, further comprising delivering electrical stimuli to the target tissue via the one or more electrodes on the positioning catheter or the ablation catheter.

7. The method of claim 1, wherein placing the first catheter in the body comprises steering the first catheter using a steering and deflection mechanism in the first catheter.

8. The method of claim 1, wherein the second catheter comprises a loop catheter, further comprising, after placing the second catheter within the lumen of the first catheter, positioning a loop of the loop catheter against the non-target body tissue and thereby stabilizing the ablation catheter with respect to the non-target body tissue.

9. The method of claim 1, wherein radiating energy from the one or more ablation elements comprises radiating ultrasound energy from an ultrasound transducer.

10. The method of claim 1, further comprising adjusting a distance between the one or more ablation elements and the target tissue by moving the ablation catheter with respect to the positioning catheter.

11. The method of claim 1, further comprising adjusting the position of the ablation catheter with respect to the target tissue by deflecting the ablation catheter.

12. A method comprising:
provinding a first catheter which is a noncontact ablation catheter and has a lumen;
providing a second catheter which fits within the lumen of the first catheter, wherein the second catheter is a positioning catheter;
placing the first catheter in a body and placing the second catheter within the lumen of the first catheter;
positioning the second catheter in contact with non-target tissue in the body;
adjusting a position of the first catheter on the second catheter in a telescoping fashion while maintaining the position of the second catheter in contact with the non-target tissue and thereby adjusting an ablation position of one or more non-contact ablation elements on the first catheter with respect to the body and a location of target tissue in the body to be ablated;
radiating energy from the one or more ablation elements on the first catheter substantially perpendicularly to an axis of the first catheter only into a predefined circumferential or semi-circumferential pattern on the target tissue without reflection and without contact between the target tissue and the one or more ablation elements; and
making one or more electrical recordings and measurements using one or more electrodes on the positioning catheter and one or more electrodes on the ablation catheter.

13. The method of claim 12, wherein a first portion of the one or more electrical recordings and measurements are made before energy is radiated to the target tissue and a second portion of the one or more electrical recordings and measurements are made after energy is radiated to the target tissue.

14. The method of claim 12, further comprising wherein the one or more electrodes on the positioning catheter are positioned on a first side of the target tissue and the one or more electrodes on the ablation catheter are positioned on an opposite side of the target tissue.

15. The method of claim 12, further comprising adjusting the position of the ablation catheter with respect to the target tissue by deflecting the ablation catheter.

* * * * *